(12) United States Patent
Li et al.

(10) Patent No.: US 10,064,288 B2
(45) Date of Patent: Aug. 28, 2018

(54) METHODS FOR CONNECTING A WIRE TO A FEEDTHROUGH PIN AND APPARATUS INCLUDING A WIRE CONNECTED TO A FEEDTHROUGH PIN BY THE METHOD

(71) Applicant: Advanced Bionics AG, Staefa (CH)

(72) Inventors: Lin Li, Valencia, CA (US); Jian Xie, Valencia, CA (US); Jeryle Walter, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 15/326,635

(22) PCT Filed: Aug. 12, 2014

(86) PCT No.: PCT/US2014/050708
§ 371 (c)(1),
(2) Date: Jan. 16, 2017

(87) PCT Pub. No.: WO2016/024953
PCT Pub. Date: Feb. 18, 2016

(65) Prior Publication Data
US 2017/0202092 A1    Jul. 13, 2017

(51) Int. Cl.
*H01R 43/04* (2006.01)
*H05K 3/32* (2006.01)
(Continued)

(52) U.S. Cl.
CPC .......... *H05K 3/328* (2013.01); *A61N 1/36032* (2013.01); *A61N 1/3754* (2013.01); *H05K 1/09* (2013.01); *H05K 1/115* (2013.01); *H05K 2201/09409* (2013.01); *H05K 2201/09709* (2013.01); *H05K 2201/1028* (2013.01); *H05K 2201/10287* (2013.01); *H05K 2201/10303* (2013.01); *H05K 2201/10424* (2013.01); *H05K 2201/10795* (2013.01); *H05K 2201/10909* (2013.01); *H05K 2201/10916* (2013.01); *H05K 2203/0169* (2013.01); *H05K 2203/0195* (2013.01); *Y10T 29/49183* (2015.01)

(58) Field of Classification Search
CPC ......... Y10T 29/49169; Y10T 29/49208; Y10T 29/49174; Y10T 29/49183; H01R 43/20; H05K 2201/1028; H05K 2201/10287; H05K 2201/10916; H05K 3/328
USPC ......... 29/862, 428, 621, 729, 747, 805, 842, 29/874, 876, 878
See application file for complete search history.

(56) References Cited

U.S. PATENT DOCUMENTS

| 3,747,051 A | 7/1973 | Swengel, Sr. et al. |
| 3,988,563 A | 10/1976 | Swengel, Sr. et al. |

(Continued)

FOREIGN PATENT DOCUMENTS

| DE | 1109232 | 6/1961 |
| DE | 19959902 A1 | 7/2001 |
| EP | 0848587 A2 | 6/1998 |

OTHER PUBLICATIONS

PCT International Search and Written Opinion dated May 4, 2015 for PCT App. Ser. No. PCT/US2014/050708.

*Primary Examiner* — Thiem Phan
(74) *Attorney, Agent, or Firm* — Henricks Slavin and Holmes (57) ABSTRACT

Methods of connecting wires (126) to feedthrough pins (104) and apparatus including wires connected to feedthrough pins.

20 Claims, 5 Drawing Sheets

(51) Int. Cl.
*A61N 1/36* (2006.01)
*A61N 1/375* (2006.01)
*H05K 1/09* (2006.01)
*H05K 1/11* (2006.01)

(56) References Cited

U.S. PATENT DOCUMENTS

| | | | |
|---|---|---|---|
| 6,172,306 B1 | 1/2001 | Downey | |
| 6,893,268 B1 * | 5/2005 | Harari | G06F 13/4068 361/679.37 |
| 8,454,396 B2 * | 6/2013 | Horn | H01F 41/076 439/874 |
| 2003/0233133 A1 | 12/2003 | Greenberg et al. | |
| 2012/0074563 A1 | 3/2012 | Iizuka | |
| 2016/0082249 A1 | 3/2016 | Thenuwara et al. | |

* cited by examiner

METHODS FOR CONNECTING A WIRE TO A FEEDTHROUGH PIN AND APPARATUS INCLUDING A WIRE CONNECTED TO A FEEDTHROUGH PIN BY THE METHOD

CROSS-REFERENCE TO RELATED APPLICATIONS

This application is the U.S. National Stage of PCT App. Ser. No. PCT/US2014/050708, filed Aug. 12, 2014.

BACKGROUND

1. Field

The present disclosure relates generally to the connection of wires to feedthrough pins.

2. Description of the Related Art

Figure 1:
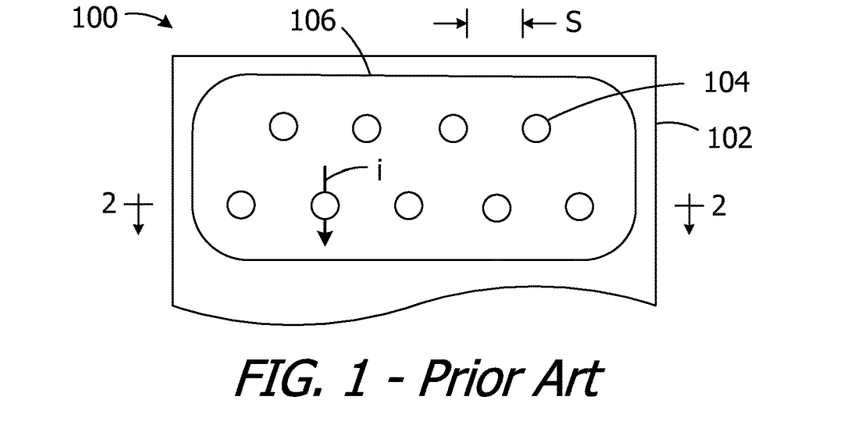
FIG. 1 is a top view of a conventional circuit board assembly.
Figure 2:
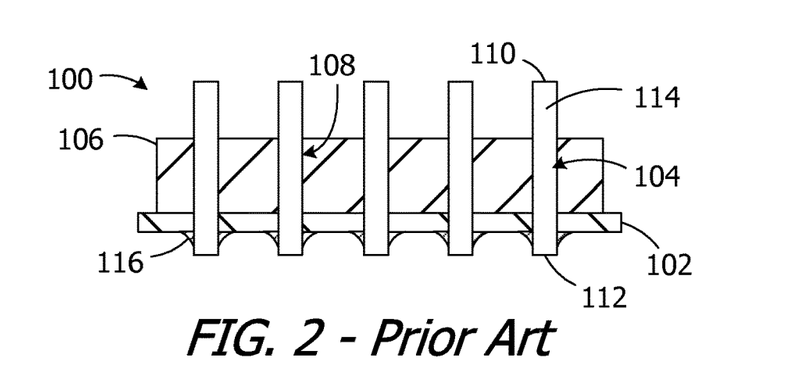
FIG. 2 is a section view taken along line 2-2 in FIG. 1.

Feedthrough pins are frequently used to connect wires to a circuit board. Referring to FIGS. 1 and 2, an exemplary printed circuit board assembly 100 includes a printed circuit board ("PCB") 102, a plurality of feedthrough pins 104, and a feedthrough 106 (e.g., a ceramic feedthrough) with a plurality of apertures 108 through which the pins extend. The feedthrough pins 104 are arranged in a two-dimensional array with the pins in one row offset from those in the other row and, in the illustrated assembly, the pins are about 0.33 mm in diameter with a space S of about 0.67 mm between adjacent pins. Each feedthrough pin 104 has first and second ends 110 and 112 and a side surface 114 that extends from the first end to the second end. As used herein in the context of a feedthrough pin, an "end" is the surface at the extremity of the pin's length, sometimes referred to herein as an "end surface," and is not a portion of the side surface. The pins 104 are connected to the associated connection points of the PCB 102 with solder 116, conductive epoxy, or other suitable instrumentalities.

The present inventors have determined that conventional methods of connecting wires to feedthrough pins are susceptible to improvement. This is especially true in those instances where the feedthrough pins are arranged in two-dimensional arrays and/or are arranged in close proximity to one another. Some conventional methods are simply incapable of connecting the wires to feedthrough pins arranged in this manner, while others are labor intensive and expensive. Referring first to FIG. 1, one conventional method of connecting a wire to a feedthrough pin is opposed gap resistance welding, which is a two sided process. Here, the side surface of a pin, a strip of platinum and a wire sandwiched between a pair of welding electrodes as current i passes from one electrode to the other and, accordingly, the electrodes must be able to access opposite sides of the pin. The resistance of the pin, platinum, wire and electrodes produces heat, thereby melting the platinum and bonding the wire to the pin. Although opposed gap resistance welding is a useful technique, the distance between the pins in the above-described closely-spaced two-dimensional array (e.g., the array illustrated in FIGS. 1 and 2) is too small to accommodate both of the electrodes. Spacing notwithstanding, in those instances wherein the portions of the pins 104 above the feedthrough 106 are relatively short, thereby decreasing the thickness of the PCB assembly, it may not be possible to properly position the electrodes on opposite sides of the pin. Similarly, access to the pins is precluded when the pins are recessed within a cavity.

Figure 3:
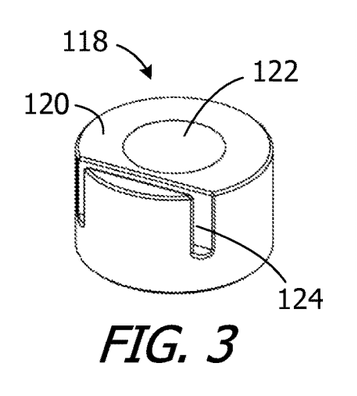
FIG. 3 is a perspective view of a crimp terminal.
Figure 4:
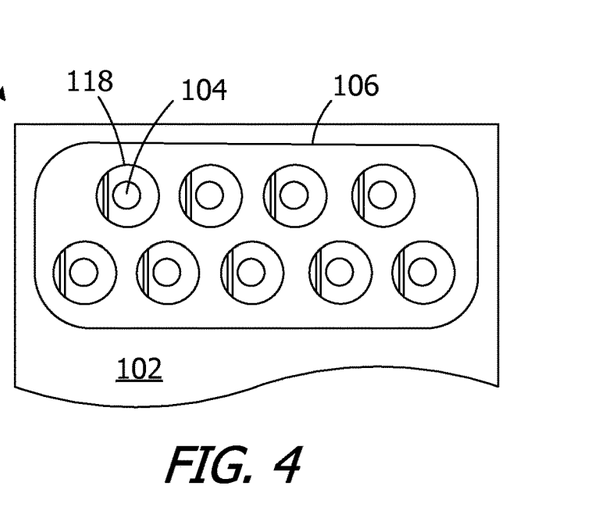
FIG. 4 is a top view of a circuit board assembly with a plurality of crimp terminals.

Turning to FIGS. 3 and 4, the present inventors have proposed welding a wire connection terminal 118 to each of the feedthrough pins 104. Each of the terminals 118 includes a cylindrical wall 120, an aperture 122 in which a portion of the associated pin 104 is located, and a slot 124. The present inventors have determined that the process of connecting a wire to a feedthrough pin 104 with a wire connection terminal 118 is relatively labor intensive and expensive. To that end, after the wire connection terminal 118 is welded to the feedthrough pin 104 in a specific orientation, a torch is used to burn the insulation off the end of the wire and the exposed conductor is placed into the slot 124. Tweezers are then used to compress the connection terminal 118 and close the slot 124, thereby crimping the wire to the feedthrough pin 104. In addition to labor, the cost of a platinum terminal is about $10, and there can be many pins and terminals in a device. In addition to being relatively labor intensive and expensive, the manual crimping process can lead to inconsistent pull-strength of the connection. The terminals also effectively reduce the spacing between adjacent feedthrough pins 104 and increase the likelihood that an exposed portion of a wire associated with one pin will contact another pin (by way of that pin's connection terminal) and cause a short.

SUMMARY

A method in accordance with one at least one of the present inventions includes the steps of positioning a portion of a wire within a connector formed from a thin strip of electrically conductive material, a portion of which is secured to an end of one of a plurality of feedthrough pins, and causing the thin strip of electrically conductive material to be secured to the portion of the wire such that the wire is electrically connected to the end of the feedthrough pin.

An apparatus in accordance with one at least one of the present inventions includes a printed circuit board assembly with a printed circuit board, a feedthrough, and a plurality of feedthrough pins, having first and second ends, that extend through the feedthrough and are connected to the printed circuit, and a plurality of wires respectively physically and electrically connected to the first ends of the plurality of feedthrough pins.

The features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

Figure 5:
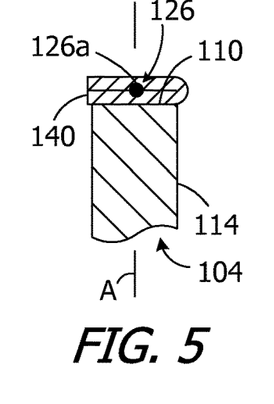
FIG. 5 is a section view showing a wire connected to a feedthrough pin in accordance with one embodiment of a present invention.

As illustrated for example in FIG. 5, the present methods involve connecting the conductor 126a of a wire 126 to the end 110 of a feedthrough pin 104. The feedthrough pin 104 may, for example, be part of the exemplary PCB assembly 100 or some other device and formed, for example, from an alloy consisting of 90% platinum and 10% Iridium. The pin end surface 110 may be flat (as shown), rounded or irregular. A relatively flat electrical joint 140 may be used to bond and electrically connect the conductor 126a to the end surface 110 of the feedthrough pin 104, as opposed to the side surface 114. As a result, the tools involved in the process need not engage the side surfaces of the pins, as do the conventional opposed gap resistance welding apparatus, and can instead operate in the axial direction (note axis A). This is a single-sided process. The feedthrough pins 104 need only be engaged at one location because the present methods employ heat and pressure to bond the wires to the pins, instead of current that flows from one electrode to another through the pins, wires and bonding material. There are a number of advantages associated with the present methods. By way of example, but not limitation, the present methods facilitate the use of two-dimensional pin arrays with closely spaced pins as well as the omission of connection terminals. The omission of connection terminals eliminates the additional expense, inconsistent pull-strength issues, and possible pin to pin shorts associate therewith. The portions of the closely spaced pins that are above the feedthrough may also be relatively short given the fact that they are engaged in the axial direction instead of from the side.

Figure 6:
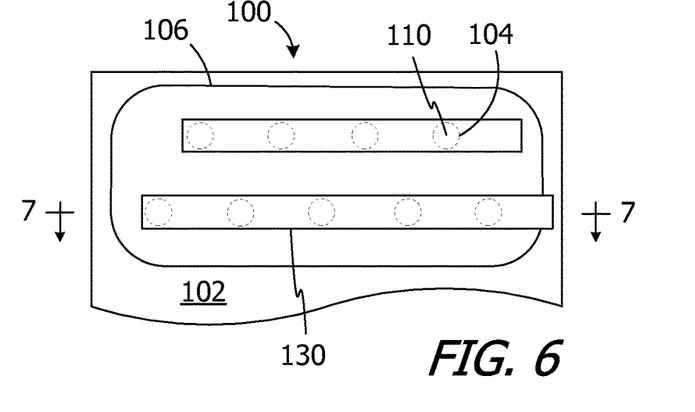
FIG. 6 is a top view showing a step in process in accordance with one embodiment of a present invention.
Figure 7:
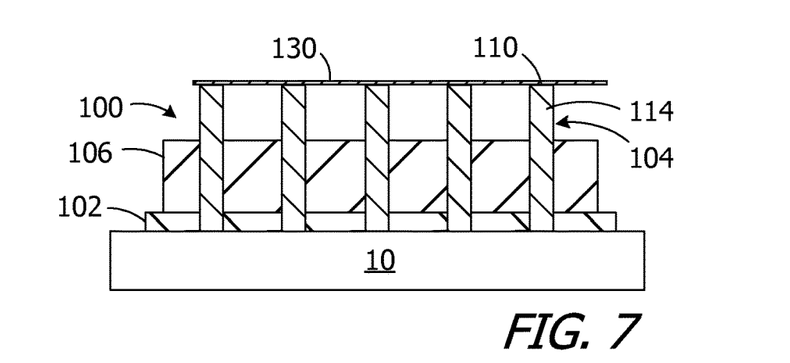
FIG. 7 is a section view taken along line 7-7 in FIG. 6.

One exemplary method of connecting wires to pins is illustrated in FIGS. 6-12. Referring first to FIGS. 6 and 7, a PCB assembly, such as the exemplary PCB assembly 100, may be supported on a support structure 10. A thin strip of electrically conductive material (or "conductive strip") 130 may be placed over each row of feedthrough pins 104 on top of the pin ends 110. In the illustrated implementation, the width of each conductive strip 130 is equal to or slightly larger than the diameter of the pin end 110, but may be slightly smaller than the diameter in other implementations. The conductive strips 130 are also slightly longer than the associated row of feedthrough pins 104. One longitudinal end of each conductive strip 130 is generally aligned with the feedthrough pin 104 at one end of the row, and the other longitudinal end extends a short distance beyond the feedthrough pin at the other end of the row.

Figure 8:
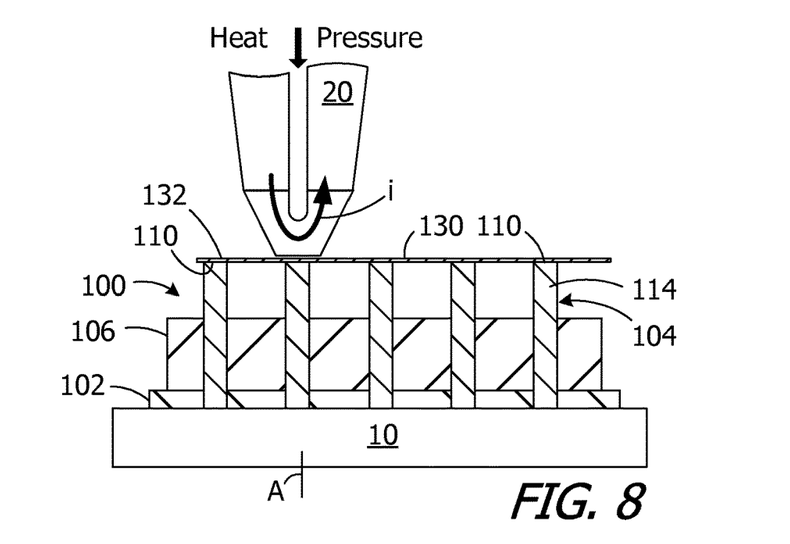
FIG. 8 is a section view showing a step in process in accordance with one embodiment of a present invention.

Turning to FIG. 8, the conductive strips 130 are then bonded to each of the feedthrough pins 104 in the associated row. In the exemplary implementation, a thermo-compression bonding process, where heat and pressure are used to weld the conductive strips 130 to each of the feedthrough pins 104 in the associated row, is employed. Bonded (or "welded") regions 132 are formed at the ends 110 of each pin 104. The heat and pressure may be applied in the axial direction by a single (i.e., one and no more than one) high resistivity metallic welding tip 20 because the process does not involve passing current though a feedthrough pins in the manner described above with reference to FIG. 1. Instead of passing current from one electrode to another to the melt the platinum strip to bond it to the pin, the present current flow remains within the welding tip 20.

Suitable electrically conductive materials for the conductive strips 130 include, but are not limited to, materials that are biocompatible and weldable to the pin material. Such materials include, but are not limited to, platinum, platinum/iridium alloys, MP35N alloy, titanium and its alloys, and gold. In the illustrated implementation, the feedthrough pins 104 in each row are about 0.33 mm in diameter, about 0.67 mm apart, and extend about 0.5 mm above the surface of the feedthrough 106, while the conductive strips 130 are about 0.025 mm thick and about 0.33 mm wide. The present feedthrough pins are not limited to those that are circular in cross-section, and other cross-sectional shapes may be employed. The first end surface 110 of each feedthrough pin 104 may be mechanically scraped prior to welding to expose a fresh metal surface for consistent and strong welds. Suitable welding tips include, but are not limited to, copper and its alloys, copper-tungsten, tungsten, and molybdenum welding tips.

Figure 9:
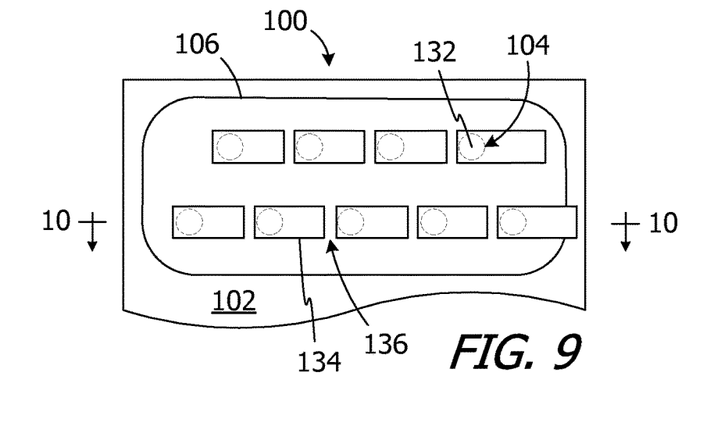
FIG. 9 is a top view showing a step in process in accordance with one embodiment of a present invention.
Figure 10:
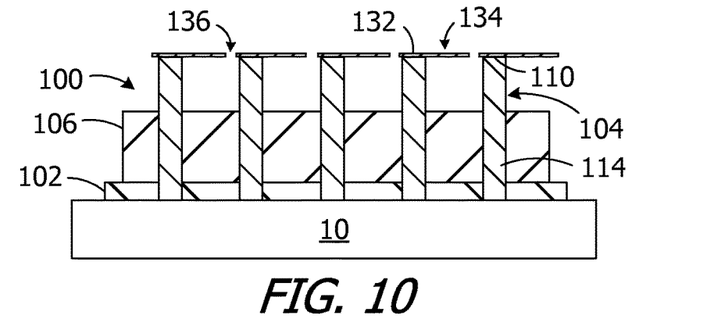
FIG. 10 is a section view taken along line 10-10 in FIG. 9.

Referring to FIGS. 9 and 10, portions of the conductive strips 130 are then trimmed to form a plurality of conductive strip segments 134 with or without gaps 136 therebetween. The gaps 136 will be present when portions of the conductive strips 130 are removed (e.g., by trimming at two adjacent locations between a pair of pins 104). Each one of conductive strip segments 134 is bonded to a respective one of the feedthrough pins 104 as a result of the process described above with reference to FIG. 8. The portions of the strips may be trimmed with, for example, small scale trimmers, cutters and scissors.

Figure 11:
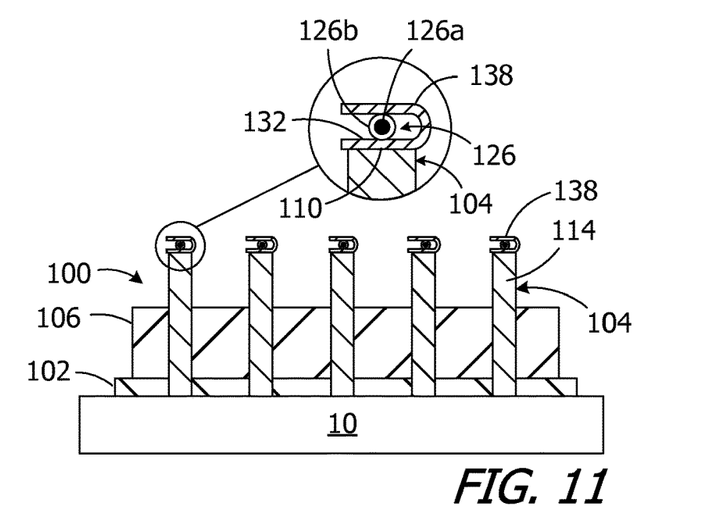
FIG. 11 is a section view showing a step in process in accordance with one embodiment of a present invention.

The conductive strip segments 134 may then, in at least some instances, be bent into a U-shape, a V-shape, or the like to form conductive connectors 138, as shown in FIG. 11. Wires 126, which have conductors 126a and insulation 126b, may be inserted into each of the connectors 138. The insulation 126b need not be removed from the portions of the wires 126 that will be connected to the pins 104. The insulation 126b will be incinerated (i.e., will burn off) when heat and pressure are subsequently applied to the top (in the illustrated orientation) of each conductive connector 138 in the manner discussed below with reference to FIG. 12 to bond the wire 126 to the end 110 of the associated feedthrough pin 104. All of the wires 126 may be inserted into the connectors 138 prior to bonding, as shown, or wires may be inserted into a connector only after the previous wire has been bonded to a pin 104.

It should be noted that, in other implementations, the conductive strip segments 134 may be bent after the wire 126 is positioned at the end 110 of the associated feedthrough pin 104. Put another way, the portions of the conductive strip segments 134 that are not bonded to the ends 110 of the feedthrough pins 104 may be folded over the wires 126 to form the connectors 138.

Heat and pressure may be applied to the conductive connectors 138 and wires 126 in a manner similar to that described above with reference to FIG. 8. For example, a single high resistivity metallic welding tip 20 may be used to apply heat and pressure in the axial direction to the conductive connectors 138 and wires 126 in the manner illustrated in FIG. 12. This process is repeated at each feedthrough pin 104. The heat and pressure burns the insulation 126b off the wires 126 and compresses the conductive connectors 138 against the conductors 126a and the ends 110 of the feedthrough pins 104, and welds the conductors 126a to the ends 110 of the pins 104, thereby forming a relatively flat electrical joint 140 that physically and electrically bonds the conductors to the ends of the pins.

Figure 12:
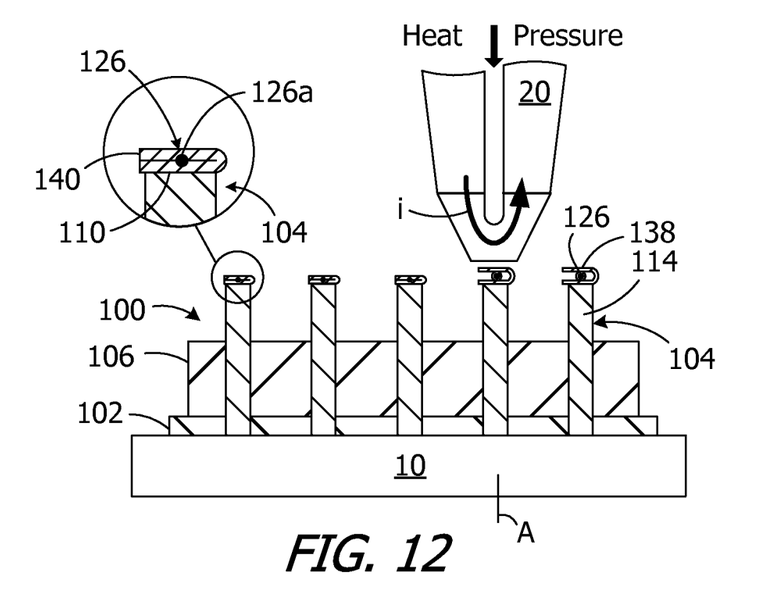
FIG. 12 is a section view showing a step in process in accordance with one embodiment of a present invention.
Figure 12A:
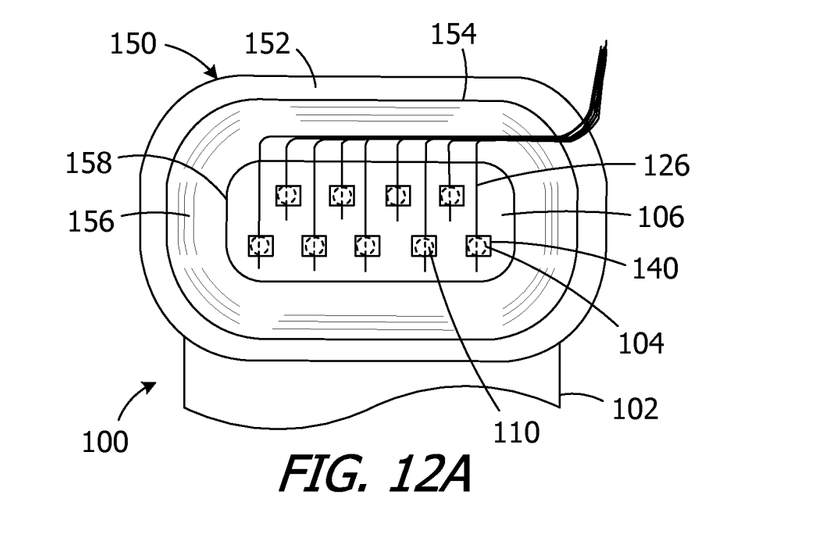
FIG. 12A is a top view of an apparatus in accordance with one embodiment of a present invention.

The present processes are also well suited for use with pins that are located at or below a surrounding surface. To that end, and referring to FIG. 12A, the exemplary PCB assembly 100 is secured to a support structure 150 which includes a top surface 152 that defines a top opening 154, and a downwardly sloping side wall 156 that terminates at a bottom opening 158. The pins 104 extend upwardly from the feedthrough 106 into a recess defined by the sloping side wall 154. The respective configurations of the PCB assembly 100 and the support structure 150 may be such that the first end surfaces 110 of the pins 104 are slightly above, or aligned with, or below the top surface 152. Despite such positioning, the electrical joints 140 may be formed in the manner described above because the process takes place at the first end surface 110 of each pin 104, instead of on opposing portions of the side surface 114, and with the welding tip 20 moving in the axial direction (see, e.g., FIG. 12).

The present inventions have application in a wide variety of devices and systems. By way of example, but not limitation, one such device is a cochlear implant that, along with a sound processor that communicates with the implant, forms an implantable cochlear stimulation system. One example of such a cochlear implant is generally represented by reference numeral 200 in FIG. 13. The exemplary cochlear stimulator 200 includes a flexible housing 202 formed from a silicone elastomer or other suitable material, an internal stimulation processor 204, a cochlear lead 206 with an electrode array 208, a positioning element (i.e., a magnet or other ferromagnetic material) 210, and an antenna 212.

Figures 13, 15:
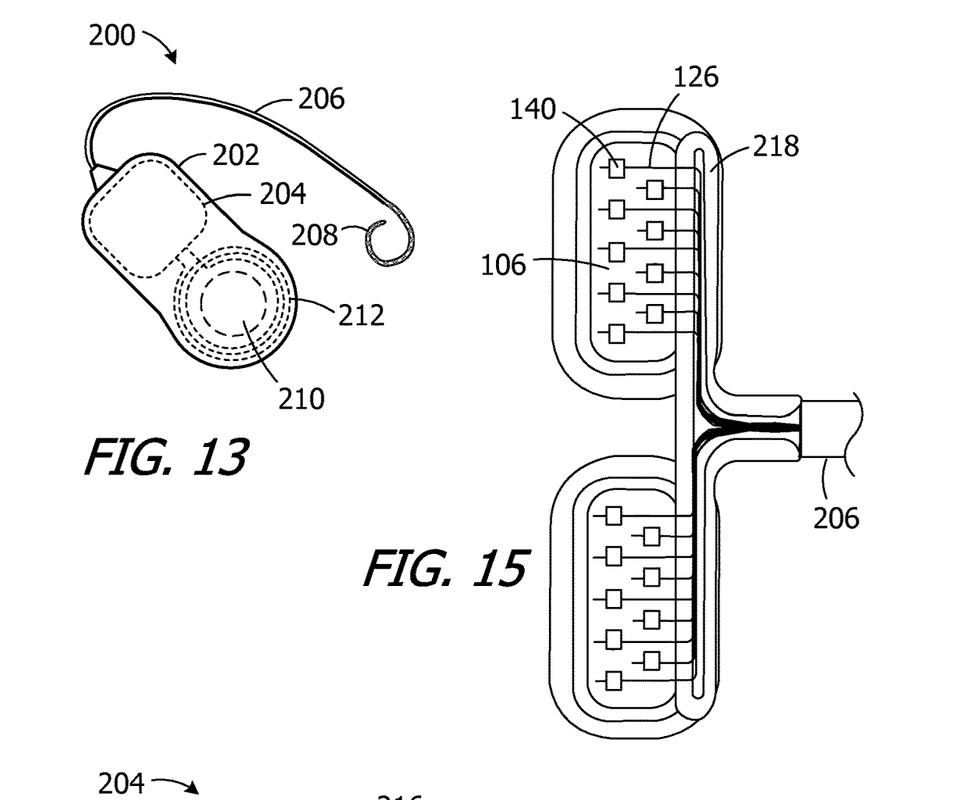
FIG. 13 is a top view of an implantable cochlear stimulator.
FIG. 15 is a top view of a portion of the implantable cochlear stimulator illustrated in FIGS. 13 and 14 showing wires bonded to pins in accordance with one embodiment of a present invention.
Figure 14:
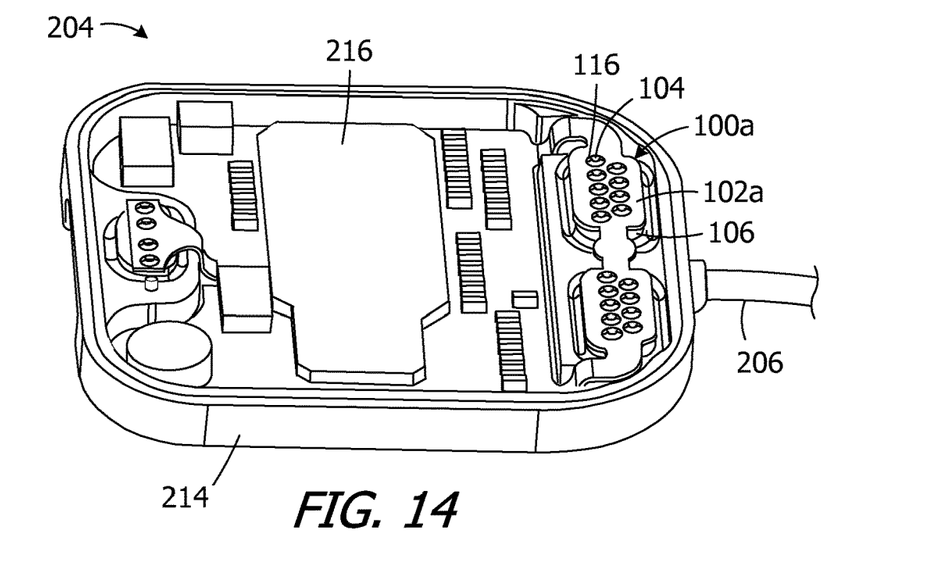
FIG. 14 is a perspective view of a portion of the implantable cochlear stimulator illustrated in FIG. 13.

As illustrated for example in FIG. 14, the exemplary stimulation processor 204 includes a case 214 (shown with the cover removed) and a PCB assembly 100a with a PCB 102a that connects various electronic components 216 to the feedthrough pins 104. The case 214 may be formed from titanium or another suitable biocompatible material. In the illustrated embodiment, there are eighteen feedthrough pins 104 that are separated into two groups of nine, with each group arranged in the two-dimensional array. Each group of nine feedthrough pins 104 is associated with a feedthrough 106 (e.g., a ceramic feedthrough) through which the pins extend. The pins 104 are connected to the associated connection points of the PCB 102a with solder 116, conductive epoxy, or other suitable instrumentalities. Turning to FIG. 15, the wires 126 (sometimes referred to as "signal wires") connect the electrodes in the array 208 (FIG. 13) to the feedthrough pins 104. The wires 126 are physically and electrically bonded to the ends 110 (FIG. 5) of respective feedthrough pins 104 by the electrical joints 140. The electrical joints 140 are formed in the manner described above with reference to FIGS. 5-12. The wires 126 may be routed through a wire carrier 218 and into the lead 206.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various steps, species and embodiments disclosed in the specification that are not already described. It is intended that the scope of the present inventions extend to all such modifications and/or additions and that the scope of the present inventions is limited solely by the claims set forth below.

We claim:
1. A method, comprising the steps of:
positioning a portion of a wire within a connector formed from a thin strip of electrically conductive material, a portion of which is mounted on an end surface of one of a plurality of feedthrough pins; and
causing the thin strip of electrically conductive material to be secured to the portion of the wire such that the wire is electrically connected to the feedthrough pin.
2. The method as claimed in claim 1, wherein
positioning a portion of a wire comprises folding the thin strip of conductive material to form the connector and positioning the portion of the wire between two sections of the folded thin strip of conductive material.
3. The method as claimed in claim 2, further comprising the step of:
prior to the folding step, welding a portion of the thin strip of electrically conductive material to the end surface of the feedthrough pin.
4. The method as claimed in claim 2, further comprising the steps of:
prior to the folding step, bonding the thin strip of electrically conductive material to the end surfaces of the plurality of feedthrough pins; and
after the bonding step, converting the thin strip of electrically conductive material into a plurality of strip segments, each of which is bonded to a respective one of the plurality of feedthrough pins.
5. The method as claimed in claim 4, wherein
bonding the thin strip of electrically conductive material comprises welding the thin strip of electrically conductive material to the end surfaces of the plurality of feedthrough pins.
6. The method as claimed in claim 4, wherein
each pin of the plurality of feedthrough pins defines a respective longitudinal axis;
bonding the thin strip of electrically conductive material comprises applying heat and pressure to the thin strip of electrically conductive material at each of the feedthrough pins in a direction that is aligned with the longitudinal axis of the feedthrough pins.
7. The method as claimed in claim 4, wherein
converting the thin strip into a plurality of strip segments comprises removing sections of the thin strips that are located between respective feedthrough pin pairs.
8. The method as claimed in claim 1, wherein
causing the thin strip of electrically conductive material to be secured to the portion of the wire comprises applying heat and pressure to the thin strip of electrically conductive material to weld the wire to the end surface of the feedthrough pin.

9. The method as claimed in claim 8, wherein
applying heat and pressure comprises generating heat with a single high resistivity weld tip, conducting the generated heat to the connector formed from the thin strip of electrically conductive material and to the feedthrough pin, and applying pressure to the connector with the single high resistivity weld tip.

10. The method as claimed in claim 8, wherein
the feedthrough pin defines a longitudinal axis and an axial direction; and
applying heat and pressure comprises applying heat and pressure in the axial direction to the connector formed from the thin strip of electrically conductive material.

11. The method as claimed in claim 1, wherein
the thin strip of electrically conductive material comprises a thin strip of material selected from the group consisting of platinum, platinum/iridium alloy, MP35N alloy, titanium, titanium alloys, and gold.

12. An apparatus made by the process of claim 1, the apparatus comprising:
a printed circuit board assembly that includes
the plurality of feedthrough pins,
a printed circuit board connected to the feedthrough pins, and
a feedthrough through which the feedthrough pins extend,
wherein the step of positioning a portion of a wire within a connector formed from a thin strip of electrically conductive material comprises
positioning a portion of each of a plurality of wires within a respective one of a plurality of connectors formed from the thin strip of conductive material, and
wherein the step of causing the thin strip of electrically conductive material to be secured to the portion of the wire such that the wire is electrically connected to the feedthrough pin comprises causing each respective one of the plurality of connectors to be secured to the respective portion of each wire such that each wire is electrically connected to the respective one of the of the plurality of feedthrough pins.

13. The apparatus of claim 12, the process further comprising the step of:
securing the printed circuit board assembly to a support structure, with a top surface that defines an opening, such that the first end surfaces of the feedthrough pins are located at or below the top surface.

14. The apparatus of claim 12, the process further comprising:
bonding the thin strip of electrically conductive material to the end surfaces of the plurality of feedthrough pins;
after the bonding step, converting the thin strip of electrically conductive material into a plurality of strip segments; and
folding the strip segments to form the connectors.

15. The apparatus of claim 12, wherein causing the thin strip of electrically conductive material to be secured to the portion of the wire comprises applying heat and pressure to the thin strip of electrically conductive material to weld the wire to the end surface of the feedthrough pin.

16. The apparatus of claim 12, wherein
each pin of the plurality of feedthrough pins defines a respective longitudinal axis; and
bonding the thin strip of electrically conductive material comprises applying heat and pressure to the thin strip of electrically conductive material at each of the feedthrough pins in a direction that is aligned with the respective longitudinal axis.

17. The apparatus of claim 12, wherein applying heat and pressure comprises generating heat with a single high resistivity weld tip, conducting the generated heat to the connector and to the feedthrough pin, and applying pressure to the connector with the single high resistivity weld tip.

18. The apparatus of claim 12, wherein
positioning the portion of each of a plurality of wires within a respective one of a plurality of connectors comprises positioning a portion of the wire, including a conductor and insulation around the conductor, within the respective connector, wherein a portion of the respective connector is secured to an end surface of one of the plurality of feedthrough pins; and
applying heat and pressure to the connector sufficient to incinerate the insulation to electrically connect the wire to the feedthrough pin.

19. The apparatus of claim 12, wherein the thin strip of electrically conductive material comprises a thin strip of material selected from the group consisting of platinum, platinum/iridium alloy, MP35N alloy, titanium, titanium alloys, and gold.

20. A method, comprising the steps of:
positioning a portion of a wire, including a conductor and insulation around the conductor, within a connector formed from a thin strip of electrically conductive material, a portion of which is secured to an end of one of a plurality of feedthrough pins; and
applying heat and pressure to the connector formed from the thin strip of electrically conductive material sufficient to incinerate the insulation to weld the wire to the end of the feedthrough pin and electrically connect the wire to the end of the feedthrough pin.

* * * * *